United States Patent [19]

Zabrecky et al.

[11] Patent Number: 5,179,199

[45] Date of Patent: Jan. 12, 1993

[54] PROTEIN PURIFICATION

[75] Inventors: James R. Zabrecky, Framingham; Nicholas C. Masiello, Milford, both of Mass.

[73] Assignee: Genzyme Corporation, Cambridge, Mass.

[21] Appl. No.: 922,067

[22] Filed: Oct. 20, 1986

[51] Int. Cl.$^5$ .............. C07K 3/28; C07K 3/22; C07K 3/20

[52] U.S. Cl. .................... 530/416; 530/412; 530/417; 530/350; 435/803; 435/69.6; 435/69.5

[58] Field of Search ............... 530/412, 416, 417, 350; 435/803, 68

[56] References Cited

U.S. PATENT DOCUMENTS

| | | | |
|---|---|---|---|
| 4,405,601 | 9/1983 | McEntire | 530/351 |
| 4,667,016 | 5/1987 | Lai et al. | 530/395 |
| 4,675,387 | 6/1987 | Korant | 530/412 |
| 4,734,362 | 3/1988 | Hung et al. | 530/412 |
| 4,748,234 | 5/1988 | Dorin et al. | 530/412 |
| 4,839,419 | 6/1989 | Kraemer et al. | 530/412 |

FOREIGN PATENT DOCUMENTS

| | | |
|---|---|---|
| 84103551.2 | 3/1984 | European Pat. Off. . |
| 0114506 | 8/1984 | European Pat. Off. . |
| 3329624 | 3/1984 | Fed. Rep. of Germany 435/68 |
| 3432196 | 3/1986 | Fed. Rep. of Germany . |
| 2032897 | 2/1987 | Japan 435/68 |
| 8605809 | 10/1986 | PCT Int'l Appl. 435/68 |
| WO8607594 | 12/1986 | PCT Int'l Appl. . |

OTHER PUBLICATIONS

Light, *BioTechniques*, 3(4), 1985, pp. 298–306.
Sofer et al., *BioTechniques*, Nov./Dec. 1983, pp. 198–203.
Hodgkinson et al., (1981), Biochem. J., 199:619–27.

*Primary Examiner*—Garnette D. Draper
*Attorney, Agent, or Firm*—Fish & Richardson

[57] ABSTRACT

A method of removing an organic solvent from a mixture that includes a compound having a polypeptide segment and the organic solvent, the method including the steps of contacting the mixture with an ion exchange resin under conditions that allow the compound to bond to the resin; and washing the resin with a first aqueous solution that elutes the organic solvent from the resin while allowing the compound to remain bound to the resin.

16 Claims, No Drawings

PROTEIN PURIFICATION

BACKGROUND OF THE INVENTION

This invention relates to the purification of Proteins, for example, those derived from cells and cell culture media.

Protein purification typically includes absorption of the protein on a reverse phase HPLC (high performance liquid chromatography) column, followed by elution of the protein with a solution containing a polar organic solvent such as ethanol, methanol, propanol, or acetonitrile. Following elution, it is often desirable to remove all organic solvent from the solution containing the protein, especially where the protein is designed for use as a pharmaceutical. Examples of methods generally used to remove the organic solvent include dialysis and vacuum evaporation.

SUMMARY OF THE INVENTION

In one aspect, the invention features a method of removing an organic solvent from a mixture that includes a compound having a polypeptide segment and the organic solvent, the method including the steps of contacting the mixture with an ion exchange resin under conditions that allow the compound to bond to the resin; and washing the resin with a first aqueous solution that washes the organic solvent from the resin while allowing the compound to remain bound to the resin.

In preferred embodiments, the method further includes the step of washing the resin with a second aqueous solution that causes the compound to elute from the resin, yielding the compound in a mixture free of organic solvent. The term free of organic solvent, as used herein, means that the aqueous eluent containing the compound has less than 5 ppm organic solvent.

The invention features, in another aspect, a method of purifying a compound having a polypeptide segment, the method including the steps of subjecting a mixture that includes the compound to a reverse phase HPLC column and eluting a sample that includes the compound with an organic solvent, contacting the sample with an ion exchange resin under conditions that allow the compound to bond to the resin, and washing the organic solvent from the resin with an aqueous solution. "Polypeptide" includes large proteins as well as polypeptides too short to be characterized as proteins.

In preferred embodiments, the compound is a protein (e.g., a biologically derived protein), and the method includes the additional step, following the eluting of the organic solvent from the resin, of eluting the compound from the resin. In other preferred embodiments the mixture is obtained from a cell culture medium and cells or cell debris in the medium, and the cells or all debris and culture medium are subjected to preliminary purification comprising ion exchange chromatography, in which the mixture is obtained by eluting the compound from an ion exchange column in an aqueous solution.

The term high performance liquid chromatography, as used herein, refers to that chromatography in which the particles (stationary phase) used as the column packing are small (between 3 and 50 microns) and regular (i.e., little variation from the selected size). Such chromatography typically employs relatively high (around 500–3500 psi) inlet pressures.

The term reverse phase HPLC, as used herein, refers to HPLC that employs a nonpolar stationary phase and a polar mobile phase.

The invention provides a simple, inexpensive, and rapid method of removing organic solvents from a protein solution. The method is non-perturbing to proteins, does not require special apparatus, and in some circumstances can even provide additional purification of the protein. The method is very efficient at removing trace amounts of organic solvent.

Other features and advantages of the invention will be apparent from the following description of the preferred embodiments thereof, and from the claims.

DESCRIPTION OF THE PREFERRED EMBODIMENTS

Ion exchange chromatography can generally be used in the invention. Such chromatography generally employs a stationary phase that has an ionically charged surface. Compounds that have ionic or ionizable functional groups of opposite charge to the stationary phase will be attracted to the stationary phase. The stronger the charge of the functional group of the compound, the more the compound will be attracted to the stationary phase, and the longer the compound will take to elute from a column containing the stationary phase. For a discussion of ion exchange chromatography, see Yost et al., Practical Liquid Chromatography: An Introduction 4, 106–11 (Perkin-Elmer 1980).

The following is an example of the use of the methods of the invention to purify erythropoieten (EPO). Aspects of the example were previously described in Beck et al., U.S. application No. 907,369, which is assigned to the same assignee as the present invention and is hereby incorporated by reference.

Recombinant human EPO can readily be purified from serum-free medium conditioned by mammalian cells producing rEPO. The purification to homogeneity generally involves the steps of: (1) clarification, concentration and dialysis of culture medium; (2) ion-exchange chromatography; (3) reverse phase HPLC; and (4) ion exchange chromatography. Steps 1 and 2 will remove from the culture medium proteases and some serum components remaining in the production medium (specifically in harvests shortly after switching the cultures from serum containing growth into serum-free production medium); steps 2 and 3 give a major purification, and step 4 is designed to remove the organic solvent used in step 3 and to elute the purified EPO in the final formulation buffer. All purification procedures are carried out at 4° C. with the exception of the RP-HPLC step, which is carried out at room temperature.

As an example, pure, homogeneous rEPO was prepared from 11.75 liters of serum-free EPO production medium harvested from the 10 liter spinner cultures described in Beck et al. EPO levels were measured throughout the purification process using the $^3$H-thy incorporation assay and an EPO RIA. All dose response curves at the different purification stages were parallel to each other and to the human urinary standard.

1) Clarification, concentration and dialysis of culture medium 11.75 liters of CES9dog conditioned serum-free media, harvested from 10 liter spinner flasks and containing approximately 700 units of EPO per ml, were made 0.01% in Tween 80, and then clarified of cell debris and microcarriers by passage through a 0.5 μm Pall Profile ™ filter cartridge at a flow rate of 2.5L/minute. The pressure of the cartridge did not exceed 20psi. The clarified media were then concentrated 10-fold and flow dialyzed into 50mM Na Acetate, pH5.0 containing 15mM NaCl, and 0.01% Tween 80 to a final conductivity of 6.90mS/cm$^2$. This was accomplished with a tangential flow system: an Amicon Spiral Ultrafiltration S10Y10 cartridge having a YM 10,000 MW cutoff membrane was used at a retention flow rate of 1.5–2L/minute, a breakthrough flow rate of 0.4–0.8L/minute, and a back pressure maintained at 25–30psi. The volume of the final concentrate was 970ml, its pH was 5.0, and its conductivity 6.90mS/cm$^2$. EPO recovery through these steps is greater than 90%.

2) Ion exchange chromatography

A screen of ion exchange resins demonstrated that relatively high ionic strength resins are best suited for the purification of EPO. In this particular example, an S-Sepharose Fast Flow column from Pharmacia was used. A 2.5cm ×12.5cm (60ml) column was equilibrated at 4° C. with 50mM Na Acetate, pH5.0, containing 15mM NaCl, and having a conductivity of 6.90mS/cm$^2$. The absorbence of the column effluent was monitored at 280nm with an in-line detector (LKB). The column was loaded with 960ml of the concentrated media at a flow rate of 5ml/minute (61.6cm/hour) and the column was washed with equilibration buffer until the absorbence returned to baseline (approximately 2 column volumes). The column was eluted with a 300ml linear salt gradient of 0.015M to 0.4M NaCl in 50mM Na Acetate, pH5.0. Fractions (6ml) were collected into tubes containing 0.15ml of 2M Tris-HCl, pH8.8. This adjusted the pH of the effluent to approximately 8.0 and gave a final Tris concentration of 0.05M. Finally, the column was washed with 0.05M Tris-HCl, pH9.0, containing 2M NaCl. EPO-containing fractions were pooled.

The S-Sepharose Fast Flow column gave an approximately 7-fold purification and a recovery of about 60%. Losses at this step are due to proteases present in the conditioned medium which are active at pH5.0 (which is the optimal pH for EPO purification with this resin). (As is described below, losses at this step can be minimized by the use of immobilized dyes or protease inhibitors.)

3) Preparative Reverse Phase HPLC

HPLC was carried out with a Waters high pressure liquid chromatography system consisting of a model 6000A solvent delivery system and a model 660 solvent programmer. A 2.2cm×25cm preparative C$_8$ column (Amicon 10μm particle size, 100Å pore size) was equilibrated at room temperature with 10mM NaPO$_4$, pH6.0 buffer. (Columns of different carbon length, e.g., C$_4$–C$_{18}$, can also be used, but are less preferred.). The pooled S-Sepharose sample was prefiltered through a 0.45μm Gelman Acrodisk filter and loaded onto the column by repeated injections using a 2ml sample loop. The column was run at 6ml/minute (71.0cm/h) and the absorbence of the effluent was monitored at 280nm. Following loading the sample, the column was washed with 10mM NaPO$_4$, pH6.0, until the absorbence returned to baseline. The column was eluted with a 2.5h linear 0% to 40% n-propanol gradient (in 10mM NaPO., pH6). One minute fractions (6ml) were collected.

Several small peaks of material absorbing at 280nm were eluted between 60 minutes and 95 minutes of the gradient and a single, sharp peak eluted between 100 minutes to 110 minutes (FIG. 8). The elution peaks were analyzed by SDS PAGE. The EPO containing fractions coincided with the large peak at 100 minutes to 107 minutes (approximately 20–25% propanol). A laser densitometer scan of the Coomassie stained SDS gel indicated that the EPO was greater than 99% pure at this stage. In this example, the C$_8$ step gave a 2-fold purification.

The recovery of immunological and of in vitro biological activity at this step was high (83%), indicating that n-propanol had no adverse effects on the in vitro biological activity.

4) Ion-exchange chromatography

To remove the propanol, the pooled activity is diluted with 10 volumes of 50 mM sodium acetate, pH 5.0, so as to lower the pH and ionic strength. The pooled activity thus diluted was applied to an S-Sepharose (a cation exchange resin sold by Pharmacia) fast flow column (2.5×4.5 cm) which has been previously equilibrated with 50 mM sodium acetate, pH 5.0, 15 mM sodium chloride. EPO bonds to the resin under these conditions. The column was washed with 5 column volumes of the same buffer to elute the propanol that is present in the sample. The column was then washed with an aqueous solution of increased ionic strength (10 mM sodium phosphate, pH 8.0, 150 mM sodium chloride), to elute EPO from the resin. The final EPO pool is 10 ml. The residual propanol is less than 5 ppm in the eluent as determined by gas chromatographic analysis.

Other Embodiments

Other embodiments of the invention are within the following claims. For example, the methods can be used with any protein that will bind to an ion exchange column, e.g. proteins containing amino acid residues having free, ionizable functional groups (e.g., lysine, arginine, histidine, aspartic acid, and glutamic acid). Moreover, any cation exchange resin which is resistant to organic solvents can be used, provided that the pH and ionic strength of the buffer used is adjusted to achieve complete bonding of the protein (such adjustments are standard in the art). Examples of other appropriate cation exchange resins include CM Cellufine (Amicon), SP-ZetaPrep cartridges (AMF), and Indion SP-53 (ASTEC).

Anion exchange resins also can be used, provided the resin is resistant to organic solvents and the pH and ionic strength of the buffer are adjusted to obtain complete bonding of the protein to the resin (such adjustments being well-known to those skilled in the art). Examples of anion exchange resins that have been used in place of S-Sepharose in step 4 of the EPO purification example are DEAE Cellufine (Amicon), DEAE Zeta-Prep (AMF), and Indion DEAE-H3 (ASTEC). All anion exchange columns were equilibrated in 10 mM sodium phosphate, pH 7.0. EPO was loaded in the same buffer, and the columns were washed with 5 column volumes of the buffer and then eluted with 2M NaCl.

We claim:

1. A method of removing an organic solvent from a mixture comprising a compound comprising a polypeptide segment and said organic solvent, said organic solvent having been introduced in a previous purifications type, said method comprising, contacting said mixture with an ion exchange resin under conditions that allow said compound to bond to said resin, and washing said resin with a first aqueous solution which contains none of said organic solvent, and that washes said organic solvent from said resin while allowing said compound to remain bound to said resin.

2. The method of claim 1 further comprising the step washing said resin with a second aqueous solution that causes said compound to elute from said resin, said compound being free of said organic solvent.

3. The method of claim 1, wherein said compound is a protein.

4. The method of claim 1, wherein said compound is a biologically derived protein.

5. A method of purifying a compound which includes a polypeptide segment from a mixture, the method comprising subjecting said mixture to a reverse phase HPLC column and eluting a sample comprising said compound and an organic solvent from said column, contacting said compound and said organic solvent with an ion exchange resin under conditions that allow said compound to bond to said resin; and washing said organic solvent from said resin with an aqueous solution.

6. The method of claim 5, wherein said compound is a protein.

7. The method of claim 5, wherein said compound is a biologically derived protein.

8. The method of claim 5 further comprising the step, following the washing of said organic solvent from said resin, of eluting said compound from said resin.

9. The method of claim 5 wherein the mixture is an aqueous mixture.

10. The method of claim 5 wherein the mixture is obtained from a cell culture medium and cells or cell debris in said medium.

11. The method of claim 10 wherein the cells or cell debris and culture medium are subjected to preliminary purification comprising ion exchange chromatography, in which the mixture is obtained by eluting the compound from an ion exchange column in an aqueous solution.

12. The method of claim 5 wherein said column is a high pressure column.

13. The method of claim 5 wherein said column is a $C_8$ column.

14. The method of claim 5 wherein said organic solvent comprises propanol.

15. The method of claim 5 wherein said ion exchange resin is a cation exchange resin.

16. The method of claim 5 wherein, prior to said ion exchange contacting step, said sample is treated to lower its pH and ionic strength.

* * * * *